(12) United States Patent
Trillo et al.

(10) Patent No.: US 7,999,011 B2
(45) Date of Patent: Aug. 16, 2011

(54) METHOD FOR CARDIOPROTECTION AND NEUROPROTECTION BY INTRAVENOUS ADMINISTRATION OF HALOGENATED VOLATILE ANESTHETICS

(75) Inventors: Raul Trillo, Long Valley, NJ (US); Ralph A. Lessor, New Providence, NJ (US); Satish Pejaver, Bridgewater, NJ (US); Navneet Puri, Bridgewater, NJ (US)

(73) Assignee: Baxter International Inc., Deerfield, IL (US)

(*) Notice: Subject to any disclaimer, the term of this patent is extended or adjusted under 35 U.S.C. 154(b) by 881 days.

(21) Appl. No.: 10/682,303

(22) Filed: Oct. 9, 2003

(65) Prior Publication Data

US 2004/0127578 A1 Jul. 1, 2004

Related U.S. Application Data

(60) Provisional application No. 60/417,934, filed on Oct. 11, 2002.

(51) Int. Cl.
*A01N 29/00* (2006.01)
*A61K 31/02* (2006.01)

(52) U.S. Cl. ........................................ 514/743

(58) Field of Classification Search .................. 514/743
See application file for complete search history.

(56) References Cited

U.S. PATENT DOCUMENTS

| | | | |
|---|---|---|---|
| 4,073,943 A | 2/1978 | Wretlind et al. | |
| 5,628,930 A | 5/1997 | Weers et al. | |
| 5,635,538 A | 6/1997 | Weers et al. | |
| 5,885,984 A | 3/1999 | MacLeod et al. | |

FOREIGN PATENT DOCUMENTS

| | | | |
|---|---|---|---|
| GB | 2350297 | * | 11/2000 |
| WO | WO 00/72820 | | 12/2000 |
| WO | WO-02/07729 | | 1/2002 |

OTHER PUBLICATIONS

Saito et al. (Reduction of Infarct Volume by Halothane: Effect on Cerebral Blood Flow or Perifocal Spreading Depression-Like Depolarizations, Journal of Cerebral Blood Flow and Metabolism, 1997, vol. 17, pp. 857-864).*
Canadian Anaesthetists' Society journal. Nov. 1978, vol. 25, No. 6, pp. 488-494.*
Gallagher et al. Anesthesia & Analgesia, 1998, vol. 86, pp. 488-492.*
Werner et al; Sevoflurane Improves Neurological Outcome After Incomplete Cerebral Ischaemia in Rats; Br J Anaesth.; Dec. 1995; pp. 756-760; 75(6).
Beirne et al; Effect of Halothane in Cortical Cell Cultures Exposed to N-methyl-D-aspartate; Neurochem Res. Jan. 1998; pp. 17-23; 23(1).
Grady et al; Correlation of Regional Cerebral Blood Flow with Ischemic Electroencephalographic Changes . . . ; Anesthiology; Apr. 1998; 88(4); pp. 892-897.
Soonthon-Brant et al; Fentanyl Does Not Increase Brain Injury after Focal Ischemia in Rats; Anesth Analg.; Jan. 1999; pp. 49-55; 88(1).
Patel et al; Isoflurane and Pentobarbital Reduce the Frequency of Transient Ischemic Depolarizations During Focal Ischemia in Rats; Anesth Analg.; Apr. 1998; pp. 773-780; 86(4).
Miura et al; Differential Effects of Anesthetic Agents on Outcome from Near Complete but Not Incomplete Global Ischemia in the Rat; Anesthesiology Aug. 1998; pp. 289-291; 89(2).
De Hert et al; Contraction-Relaxation Coupling and Impaired Left Ventricular Performance in Coronary Surgery Patients; Anesthiology Mar. 1999; pp. 748-757; 90(3).
De Hert et al; Length-Dependent Regulation of Left Ventricular Function in Coronary Surgery Patients; Anesthiology Aug. 1999; pp. 379-387; 91(2).
De Hert et al; The Effects of Beta-Adrenergic Stimulation on the Length-Dependent Regulation of Myocardial . . . ; Anesth Analg. Oct. 1999; pp. 835-842; 89(4).
Engelhard et al; Desflurane and Isoflurane Improve Neurological Outcome after Incomplete Cerebral Ischaemia in Rats; Br J Anaesth. Sep. 1999; pp. 415-421; 83(3).
Belhomme et al; Evidence for Preconditioning by Isoflurane in Coronary Artery Bypass Graft Surgery; Circulation Nov. 9, 1999; pp. II-340-II-344.
Wenker Oliver C; Review of Currently Used Inhalation Anesthetics : Part I; The Internet Journal of Anesthiology 1999; vol. 3(2).
Wenker Oliver C; Review of Currently Used Inhalation Anesthetics : Part II; The Internet Journal of Anesthiology 1999; vol. 3(3).
Kimbro et al; Isoflurane and Pentobarbital Reduce AMPA Toxicity In Vivo in the Rat Cerebral Cortex; Anesthesiology Mar. 2000; pp. 806-812; 92(3).
Kawaguchi et al; Isoflurane Delays but Does Not Prevent Cerebral Infarction in Rats Subjected to Focal Ischemia; Anesthesiology May 2000; pp. 1335-1342; 92(5).
Roscoe et al; Isoflurane, but Not Halothane, Induces Protection of Human Myocardium via Adenosine A1 Receptors . . . ; Anesthiology Jun. 2000; pp. 1692-1701; 92(6).
Toller et al; Sarcolemmal and Mitochondrial Adenosine Triphosphate-Dependent Potassium Channels; Anesthiology Jun. 2000; pp. 1731-1739; 92(6).
Nellgard et al; Anesthetic Effects on Cerebral Metabolic Rate Predict Histological Outcome From . . . ; Anesthiology Aug. 2000; pp. 431-436; 93(2).

(Continued)

*Primary Examiner* — Sreeni Padmanabhan
*Assistant Examiner* — Samira Jean-Louis
(74) *Attorney, Agent, or Firm* — Marshall, Gerstein & Borun LLP (57) ABSTRACT

Provided is a method of treating a patient having a tissue that is subject to an ischemic event. The method is conducted by parenterally administering a formulation containing a halogenated volatile anesthetic in an amount effective to improve the tissue's resistance to or tolerance of the ischemic event. In preferred embodiment of the invention, the amount of the formulation administered to the patient is sub-anesthetic. The formulation can be administered prior to, concurrently with, or after the ischemic event. The method can be used, for example, for treatment of patients having myocardial or neuronal tissue that is subject to an ischemic event.

13 Claims, 5 Drawing Sheets

OTHER PUBLICATIONS

Hans et al; Neuroprotection with Anaesthetic Agents; Current Opinion in Anaesthiology 2001; pp. 491-496; vol. 14.
Haroun-Bizri et al; Does Isoflurane Optimize Myocardial Protection During Cardiopulmonary Bypass? J Cardiothorac Vasc Anesth. Aug. 2001; pp. 418-421; 15(4).
Hanouz et al; Mechanisms of Desflurane-Induced Preconditioning in Isolated Human Right Atria in Vitro; Anesthiology Jul. 2002; pp. 33-41; 97(1).
De Hert et al; Sevoflurane but Not Propofol Preserves Myocardial Function in Coronary Surgery Patients; Anesthiology Jul. 2002; pp. 42-49; 97(1).
Warltier et al; Anesthetic Preconditioning; Serendipity and Science; Anesthiology Jul. 2002; pp. 1-3; 97(1).
Cuignet et al; A Second-Generation Blood Substitute (Perflubron Emulsion) Increases the Blood Solubility of Modern Volatile . . . ; Anesth Analg Aug. 2002; pp. 368-372.
Park KW; Cardiovascular Effects of Inhalational Anesthetics; Int. Anesthiol Clin; Winter 2002; pp. 1-14; 40(1).
De Hert et al; Effects of Propofol, Desflurane, and Sevoflurane on Recovery of Myocardial Function . . . ; Anesthiology Aug. 2003; pp. 314-323; 99(2).
Conzen et al; Sevoflurane Provides Greater Protection of the Myocardium Than Propofol in Patients Undergoing Off-Pump . . . ; Anesthiology Oct. 2003; pp. 826-833; 99(4).
Engelhard et al; The Effect of Sevoflurane and Propofol on Cerebral Neurotransmitter Concentrations During Cerebral Ischemia in Rats; Anesth Analg. Oct. 2003, pp. 1155-1161; 97(4).
Faithfull et al., "Protection against myocardial ischemia by prior hemodilution with fluorocarbon emulsions," *Br. J. Anaesth.*, 60:773-778 (1988).
Supplementary European Search Report for corresponding European application No. EP03774657, dated Feb. 28, 2008.
"Effect of halothane and sevoflurane on myocardial function and oxygen-derived free radicals during ischemia and reperfusion," Chinese J. Pathophysiology, 15(4):313-314 (1999) (abstract).
International Search Report for PCT/US03/31826, dated Jul. 7, 2004.
Japanese Office Action for JP Application No. 2004-543499, dated Jun. 8, 2010.
Japanese Office Action for JP Application No. 2004-543499, dated Jun. 8, 2010. (English Translation).
Akazawa et al., Kyoketsushin ni oyobosu Sebofururen no eikyo (Effects of Sevoflurane on ischemic heart), *Masui (Anesthesia)*, 42:S66 (Oct. 1993).
Akazawa et al., Kyoketsushin ni oyobosu Sebofururen no eikyo (Effects of Sevoflurane on ischemic heart), *Masui (Anesthesia)*, 42:S66 (Oct. 1993). (English Translation).
Cryonics Issue #17, Meat, Dec. 1981. Selected contents: Cryonics. Downloaded from the Internet at: <http://www.alcor.org/cryonics/cryonics8112.txt>.
Imai et al., Kyunyumasuiyaku no kankyoketsu-saikanryushogai ni oyobosu eikyo (The effect of inhalation anesthetics on ischemia-reperfusion injury in liver), *Masui (Anesthesia)*, 42: S71 (Oct. 1993).
Imai et al., Kyunyumasuiyaku no kankyoketsu-saikanryushogai ni oyobosu eikyo (The effect of inhalation anesthetics on ischemia-reperfusion injury in liver), *Masui (Anesthesia)*, 42: S71 (Oct. 1993). (English Translation).
Kanaya et al., Isofururen no saikanryu shinkintaisha ni oyobosu eikyo (Effects of isoflurane anesthesia on myocardial metabolism in reperfused heart), Masui (Anesthesia), 42: S326 (Oct. 1993).
Kanaya et al., Isofururen no saikanryu shinkintaisha ni oyobosu eikyo (Effects of isoflurane anesthesia on myocardial metabolism in reperfused heart), Masui (Anesthesia), 42: S326 (Oct. 1993). (English Translation).
Kon et al., Isofururene kankyoketsu-saikanryushogai ni oyobosu eikyo (The effects of isoflurane on ischemia-reperfusion injury in liver), Masui (Anesthesia), 42:S261 (Oct. 1993).
Kon et al., Isofururene kankyoketsu-saikanryushogai ni oyobosu eikyo (The effects of isoflurane on ischemia-reperfusion injury in liver), Masui (Anesthesia), 42:S261 (Oct. 1993). (English Translation).
Toda et al., Sebofururen no kandomyaku kakuchosayo (Vasodilator effect of sevoflurane in coronary arteries), *Masui (Anesthesia)*, 42:S339 (Oct. 1993).
Toda et al., Sebofururen no kandomyaku kakuchosayo (Vasodilator effect of sevoflurane in coronary arteries), *Masui (Anesthesia)*, 42:S339 (Oct. 1993). (English Translation).
European Office Action for EP 03 774 657.5-2123, dated Mar. 23, 2010.
Korean Office Action from corresponding Korean Application No. 10-2005-7006049, dated Oct. 22, 2010.
Kitaguchi et al., Effects of sevoflurance on cerebral circulation and metabolism in patients with ischemic cerebrovascular disease, *Anesthesiology*, 79:704-9 (1993).

* cited by examiner

* significantly different from control group (p < 0.05).

METHOD FOR CARDIOPROTECTION AND NEUROPROTECTION BY INTRAVENOUS ADMINISTRATION OF HALOGENATED VOLATILE ANESTHETICS

This application claims the benefit of priority of U.S. Provisional Patent Application Ser. No. 60/417,934, filed Oct. 11, 2002, the disclosure of which is hereby incorporated by reference as if fully set forth herein.

The present invention relates to a method for improving tissue tolerance of and resistance to an ischemic event in a patient, preferably a human, by administering an intravenous formulation containing an effective amount of a halogenated volatile anesthetic (HVA) to the patient.

Preclinical and clinical evidence indicates that HVAs (e.g., halothane, methoxyflurane, isoflurane, enflurane, desflurane and sevoflurane) confer a secondary benefit of cardioprotection during ischemic states. This benefit is not seen with parenterally administered anesthetics agents such as propofol and barbiturates. There is also an increasing awareness that the HVAs decrease cerebral oxygen consumption and can also confer neuroprotection during ischemia of nervous tissue by this mechanism as well as other mechanisms.

While these improvements to tissue tolerance of ischemia are very desirable, current volatile anesthetics are generally only administered by inhalation, requiring the use of an anesthesia machine in a controlled environment such as an operating room. To provide a wider patient population wherein these anesthetics can be more conveniently administered, a method of administering HVAs in other areas of the hospital as well as outside the hospital would be highly desirable.

Parenteral administration, especially i.v. administration of HVAs has been problematic due to a number of factors related to their combination with blood plasma. These anesthetics have poor water-solubility and their i.v. administration using conventional formulation is not well tolerated, resulting in severe local reactions. In addition, gas embolisms may occur upon i.v. administration of HVAs whose boiling points are at or below normal human core body temperature. More robust parenteral formulations have been proposed that have been used for conventional anesthesia. However, the art has not recognized the desirability of using such parenteral formulations for tissue protection, and in particular has not recognized the desirability of use outside the orbit of surgical anesthesia to achieve such tissue protection.

SUMMARY OF THE INVENTION

In one aspect the invention relates to a method of treating a patient having a tissue such as from heart, brain, vasculature, gut, liver, kidney and eye that is subject to an ischemic event. The method includes parenterally administering a formulation containing a halogenated volatile anesthetic to the patient in an amount effective to improve the tissue's resistance to or tolerance of the ischemic event. In a preferred embodiment, the amount of formulation administered to the patient is sub-anesthetic.

In one preferred embodiment, the method is conducted with a formulation that includes an emulsification adjuvant and an emulsifier in addition to the halogenated volatile anesthetic.

Using the method, the administration of the formulation to the patient can be conducted prior to, concomitantly, and/or after the ischemic event. The ischemic event can be associated with, for example, aortic aneurysm repair, multiple trauma, peripheral vascular disease, renal vascular disease, myocardial infarction, stroke, sepsis and multi-organ failure.

The administration of the formulation can be conducted by bolus administration of the formulation or by continuous infusion of the formulation. Preferably, the halogenated volatile anesthetic is selected from the group consisting of desflurane, isoflurane, enflurane, halothane and sevoflurane.

A preferred aspect of the invention relates to a method of treating a patient having myocardial tissue that is subject to an ischemic event. The ischemic event can be associated, for example, with angioplasty, coronary artery bypass surgery, cardiac catheterization and unstable angina. The method includes parenterally administering a formulation containing a halogenated volatile anesthetic to the patient in an amount effective to improve the myocardial tissue's resistance to or tolerance of the ischemic event. In a preferred embodiment, the amount of formulation administered to the patient is sub-anesthetic. The halogenated volatile anesthetic in the formulation can be, for instance, desflurane, isoflurane, enflurane, halothane or sevoflurane.

Another preferred aspect of the invention relates to a method of treating a patient having myocardial tissue that is subject to myocardial infarction. The method includes parenterally administering a formulation including a halogenated volatile anesthetic to the patient in an amount effective to improve the myocardial tissue's resistance to or tolerance of the myocardial infarction. In a preferred embodiment, the amount of formulation administered to the patient is sub-anesthetic, and the administration is conducted by i.v. administration. The halogenated volatile anesthetic in the formulation is preferably selected from sevoflurane, enflurane and isoflurane.

Another aspect of the invention relates to a method of treating a patient having neuronal tissue that is subject to an ischemic event. For example, the ischemic event can be selected from the group consisting of aortic aneurysm repair, carotid endarterectomy, cerebral arteriography, stroke, impending stroke and transient ischemic attacks. The method includes parenterally administering a formulation that contains a halogenated volatile anesthetic to the patient in an amount effective to improve the neuronal tissue's resistance to or tolerance of the ischemic event. Preferably, the amount of the formulation administered is sub-anesthetic.

DEFINITIONS

The following terms shall have, for the purposes of this application, the respective meanings set forth below.

"Bolus dose" means an administration of a formulation that is conducted over a relatively short time period as will be recognized by those of skill, such as about 5 minutes or less.

"Effective amount" when used to describe a dose of an anesthetic, refers to an amount of HVA effective to improve a tissue's resistance to or tolerance of an ischemic event.

"Improve a tissue's resistance to and tolerance of an ischemic event" when used to describe the effects of treatments, refers to treatments that (i) reduce the amount of necrotic tissue that would be expected after the ischemic event; (ii) reduce the chemical signature (e.g., pH, CPK level, troponin level, S-100 level, nitric oxide, inducible nitric oxide synthetase) of such event; or (iii) otherwise provide a pharmacological, physiological or medicinal indicator of reduced ischemic injury, such as a reduction in the expected injury related to the structural, mechanical or behavioral function of an ischemic organ.

"Infusion dose" means an administration of a formulation that is conducted over a relatively extended time period, as will be recognized by those of skill, such as greater than about two minutes, preferably greater than five minutes. This administration can occur before, during or after the ischemic injury.

"Minimum alveolar concentration (MAC)", as is known in the art, is the alveolar concentration of an anesthetic, administered by inhalation at a pressure of 1 atmosphere, that prevents movement in 50% of patients in response to a painful stimuli. The MAC is age-dependent; it may be affected by a patient's medical condition; and it may also be affected by other pharmaceutical agents that are administered to the patient. In the context of intravenous administration of HVAs, the term "MAC" or "MAC-equivalent" is intended to mean an intravenous dose which produces the same blood plasma concentration of an anesthetic agent as that attained by inhalational administration of a gaseous concentration of anesthetic which prevents such movement in 50% of patients.

"Patient" means an animal, preferably a mammal and more preferably a human.

"Sedation" indicates a level of relaxation of a patient such that with a sufficient stimulus the patient can be aroused.

"Sub-anesthetic dose" refers to an anesthetic dose wherein at least one of the following applies: (a) a dose at which pain reduction is insufficient to eliminate a patient's response to a surgical stimulus or injury in the majority of patients; or (b) wherein the dose is below 1 MAC or MAC-equivalent, more preferably below 0.75 MAC or MAC-equivalent. In a preferred embodiment, a sub-anesthetic dose refers to (b). While the MAC value can vary with other parameters, a sub-anesthetic dose can be approximated by the one of skill in the art (e.g., clinician) by a value appropriate for the patient's age, size and species. The plasma concentration dosed to the patient can be estimated by monitoring the concentration of HVA exhaled by the patient (using appropriate partition coefficients and corrections for non-equilibrium mass-transfer) or by direct sampling of the blood.

"% V/v" refers to the percentage of the specified component on the basis of the volume of the component as a percentage of the total volume of the emulsion.

"% W/v" refers to the percentage of the specified component on the basis of the weight of the component as a percentage of the total volume of the emulsion.

DETAILED DESCRIPTION OF THE INVENTION

The invention provides methods for treating a patient with a tissue susceptible to damage from an ischemic event (such as myocardial or neuronal tissue) with an HVA to improve the tissue's tolerance to the ischemic event. The methods preferably relate to administering a formulation containing the HVA to a patient intravenously prior to or during the ischemic event. Among other things, the methods provide a convenient procedure for rapidly preconditioning the tissue to resist an ischemic event.

In addition to providing a more convenient method of administration, intravenous administration of HVA's can provide a more rapid induction of the protective effect than the administration by inhalation. In addition, intravenous administration of HVAs avoids constriction of the patient's airway. Moreover, intravenous administration precludes airway irritation associated with some HVA's; reduces the release of HVAs to the treatment environment; eliminates the requirement for a vaporizer to administer the agent; allows administration inside or outside a hospital setting; facilitates the administration of HVAs before, during or after the ischemic event; and reduces the need for personnel trained in the administration of inhaled anesthetics.

Damage to tissue as a result of ischemia can occur concomitantly with the deficiency of the blood supply to the tissue, and it can also occur subsequent to the ischemic insult, for example, due to reperfusion of the damaged tissue. Tissues that are particularly susceptible to ischemic events include myocardial, vascular and neuronal tissue (particularly cerebral tissue). Other tissues that are susceptible to ischemia include tissue from the gut, liver, kidney and eye.

In one preferred aspect, the patient to be treated is in need of cardioprotection. In some embodiments this need may arise due to the inherent risk of ischemia in cardiac therapeutic or diagnostic procedures. For example, ischemic states may arise during such therapeutic procedures as cardiac and cerebral angioplasty (with or without stent placement), cerebral embolization and during coronary artery bypass surgery (with use of a bypass pump or without). Ischemic states may also arise during diagnostic procedures during such as catheterization and cerebral arteriography. In addition, the need for cardioprotection may arise due to certain physiological disorders such as unstable angina, during trauma or periods of cardiac arrest, or during organ harvest or transplantation.

For surgical and diagnostic procedures where a need for cardioprotection is indicated, a parenteral formulation can be given immediately prior, during or immediately after the surgical or diagnostic procedure is conducted to improve the tolerance of the tissue to ischemia.

The parenteral formulation can also be administered in emergency situations where cardioprotection is indicated such as treatment of patients with ongoing myocardial infarction. I.v. administration of an enflurane, isoflurane or sevoflurane formulation prior to coronary artery occlusion is now shown to confer a significant reduction in the myocardial infarct size in rabbits over vehicle-treated animals (see Example 2).

In another preferred aspect, the patient to be treated is in need of neuroprotection. Such need arises, for example, from certain procedures where interruption of arterial blood flow is likely. Non-limiting examples of such procedures are carotid endarectomy, aortic aneurysm repair, cerebral angioplasty, cerebral stenting and cerebral arteriography. In addition, disorders such as stroke, transient ischemic attacks or impending stroke (amarosis fugax) are candidate conditions for treatment using the method of the invention. Where stroke giving rise to a risk of secondary stroke occurs, or another condition giving rise to a risk of stroke within hours or days occurs, the method can be applied to diminish such risk. In addition, the formulation can be administered for emergency use for a patient suffering from an ongoing stroke to improve the tissue's resistance to or tolerance of the stroke.

Those of skill in the art will recognize circumstances associated with increased risk of other ischemic tissue injury. Such disease states include mesenteric artery insufficiency, renal artery stenosis, hepatic vein thrombosis, peripheral vascular insufficiency, multiple trauma, sepsis and multi-organ system failure.

In the inventive method, the doses of the formulation that are administered to the patient are dependent on the condition of the patient and the treatment options that are being pursued. In many instances, it is desirable to administer the formulation in doses that are sub-anesthetic so that primarily only a tissue protective effect is provided by the HVA. However, there are instances in which sedation is desired along with tissue protection. For example, in instances such as some of the above-described surgical and diagnostic procedures where the procedures require the patient to be sedated, the HVA may fulfill a dual role, providing tissue protection from ischemia and providing sedation. The HVA is administered in higher doses to effect both sedation and tissue protection to the patient. A sub-anesthetic dose of an HVA can also be delivered intravenously to provide tissue protective effects while a dose of another anesthetic is administered. In instances in which both tissue protection and anesthesia are desired, additional medications, such as muscle relaxants, sedatives and analgesics, may also be administered as is commonly done during administration of sedation.

In embodiments of the method, wherein the dosages of the formulation administered are to provide both tissue protection and sedation, the practitioner can rely on anesthesia protocols that are well-known in the art that ensure adequate loss of sensation to a surgical stimulus or injury. Dosages that ensure effective sedation are higher than those required for effective tissue protection, so that administration of the formulation at these higher doses effectively treats both of the needed indications.

In other embodiments of the method, it is desirable to administer smaller amounts of the formulation that are sub-anesthetic so that primarily only a tissue protective effect is provided by the treatment. Such administrations may be warranted in procedures such as diagnostic procedures, where there is a need to preserve the patient's sensation to a stimulus from the practitioner or, the formulation of the invention is used to assure the tissue protective effect, while another anesthetic formulation achieves a net anesthetic effect. Those of skill in the art will recognize other embodiments where it is desirable to parenterally administer sub-anesthetic dosages of the formulation, such as emergency medical situations where the administration provides a tissue protective effect. Such administration can be performed, for example, by emergency medical technicians prior to treatment of the patient by hospital emergency room personnel (e.g., during transport of the patient). Alternatively, the parenteral HVA may be used in a sub-anesthetic amount in conjunction with another class of anesthetic such as an opioid or propofol, or another inhalation HVA.

Administration of sub-anesthetic effective amounts of enflurane, isoflurane sevoflurane, for instance, is now shown to provide myocardial protection in rabbits. Experiments with rabbits indicate that myocardial protection can be seen with dosages as low as 0.15 to 0.17 MAC-equivalents (measured as blood concentration) (see Example 2).

The formulation can be administered using bolus dosing or infusion dosing depending on the needs of the patient. Of course, the formulation can also be administered using other intravenous injection techniques such as a slow i.v. push procedures or by means of a continuous infusion pump before, during or after the ischemic event.

For bolus i.v. administration of the formulation, the amount of the HVA delivered to the patient is dependent on the selection of the particular HVA, and whether the HVA is to serve an anesthetic role. For isoflurane, for example, dosages of about 10 mg/kg to 200 mg/kg are generally used, although higher amounts can be used when the patient is intubated. It will be apparent to those of skill in the art that the dosage level required to induce anesthesia in any given patient will vary depending on the individual patient's medical state, on the patient's response to the HVA used as well as other factors. Thus, the dosages described herein for inducing anesthesia are merely exemplary and not limiting. Generally, a dose of isoflurane that would provide tissue protection and anesthetize the patient would be above about 125 mg/kg. For example, for isoflurane an anesthetic-effective dose would be about 145 mg/kg, which if the emulsion is formulated with 10% v/v isoflurane, would correspond to 1.0 mL/kg of the formulation. When a patient is to be given an amount of the isoflurane effective for tissue protection (e.g., cardioprotection, neuroprotection), but an amount that is sub-anesthetic, a dose of less than about 125 mg/kg of isoflurane is typically administered, for example, about 110 mg/kg. Actual sub-anesthetic dosages will depend on patient age, state and responsiveness to anesthetic agents, other medications used, and a number of other factors. Table 1 (below) provides preferred dosage ranges for isoflurane and desflurane. Preferred bolus dosages for other HVAs can be readily calculated by those of skill in the art based on the relative potencies of the HVAs.

For infusion dosing of the formulation, dosages of isoflurane, for example, at about 2 mg/kg/min to 20 mg/kg/min are useful for tissue protection from ischemic events. Administration of the formulation is preferably over the period useful in producing preconditioning of the tissue, for example, about 15 minutes. Shorter periods, in some cases, for example 5 minutes, may also be sufficient. A rate of infusion for isoflurane that would provide both tissue protection and anesthesia to a patient would be above about 8 mg/kg/min, for example, about 12 mg/kg/min. When a patient is to be given an amount of isoflurane effective for tissue protection (e.g., cardioprotection, neuroprotection) but an amount that is sub-anesthetic, than isoflurane is preferably administered at rates that are less than about 8 mg/kg/min. Table 1 (below) illustrates preferred dosage rates for isoflurane and desflurane. Preferred infusion rates for other HVAs can be readily calculated by those of skill in the art based on the relative potencies of the HVAs.

TABLE 1

|  | Isoflurane | Desflurane |
| --- | --- | --- |
| Bolus dose range, mg/kg (Non-intubated patient) | 10–200 | 30–800 |
| Preferred Bolus range, mg/kg | 50–150 | 100–500 |
| Infusion rate range, mg/kg/min | 2–50 | 6–250 |
| Preferred infusion rate range, mg/kg/min | 3–15 | 15–60 |

Typical HVA's that can be used in the inventive method include halothane, methoxyflurane, isoflurane, enflurane, desflurane and sevoflurane. Preferably the HVA is isoflurane, halothane, enflurane or sevoflurane. The emulsion contains the HVA in a range of about 1% to 30% v/v.

The HVA may be administered in any formulation that achieves delivery of an amount of HVA effective to improve the tissue's resistance to or tolerance of the ischemic event. Formulations suitable for the invention include, for example, formulations containing oils and surfactants, and liposomal formulations.

One preferred i.v. formulation that is used in the method is an emulsion that contains an HVA, an emulsification adjuvant and one or more emulsifiers (also known as emulsion stabilizers). The emulsion generally contains a vehicle which is typically a water component. Optionally the emulsion may contain additional components such as a tonicifier and a base.

The emulsion contains an emulsification adjuvant in which the HVA is soluble, and preferably in which the HVA is highly soluble. Suitable adjuvants include, for example, soy bean oil or a perfluorocarbon solvent (e.g., perfluorodecalin). Other emulsification adjuvants having the properties of the soybean oil or perfluorocarbon solvents are apparent to those skilled in the art and can be used in the formulation. A useful concentration range for the emulsification adjuvant is about 5% to 30% w/v, and a preferred range is 10% to 20% w/v. The total volume of the HVA and emulsification adjuvant is preferably 40% w/v or less.

The anesthetic formulation also includes an emulsifier, which among other things, assists in stabilizing the emulsion. For example, phospholipids such as lecithin can be used in amounts that are effective to stabilize the emulsion. Lecithin, for example, is typically used in amount from about 0.2% to 3.6% w/v.

The vehicle for the formulation is typically a water component, such as a dilute aqueous buffer or water neat. When water neat is used as the vehicle, a base, e.g., sodium hydroxide, can be used to adjust the pH of the formulation to a suitable level, such as from about 6 to 9.

In some embodiments it may be beneficial to include additional components such as a tonicifier. The tonicifier may be sodium chloride or a polyol, e.g., glycerol, that if present, is used in the range of about 1 to 4% w/v.

One particularly preferred formulation for use in the method uses soybean oil as the emulsification adjuvant, lecithin in about 2.4% w/v as the emulsifier, glycerol as a tonicifier, water as the injection vehicle and an HVA selected from isoflurane, enflurane and sevoflurane.

Another particularly preferred formulation uses a perfluorocarbon such as perflurodecalin as the emulsification adjuvant, a phospholipid in about 3.6% w/v as the emulsifier and water as the vehicle. For example, fluorocarbon emulsions such as those described in U.S. Pat. Nos. 5,628,930 and 5,635,538 (which are both hereby incorporated by reference) to Weers et al. can be used. An HVA selected from isoflurane, enflurane and sevoflurane is preferably added to the formulation.

The emulsion formulation can be prepared by any method that yields a stable and sterile formulation. In one preferred method for preparing the formulation, suitable quantities of the emulsification adjuvant (e.g., soy bean oil) and the emulsifier (e.g., lecithin) are combined, using any additional means such as heat or agitation to hasten the dissolution process. An appropriate quantity of the HVA is then dissolved in the adjuvant-emulsifier mixture to form the oil phase of the emulsion. Separately, the aqueous phase of the emulsion is prepared using a solution containing a water component to be used in the formulation. At this point, the optional tonicifier component (e.g., sodium chloride, glycerol) can be combined with the water component. The oil phase is added to the water phase with mixing to form the primary emulsion. The pH of the emulsion can be adjusted with a base (e.g., sodium hydroxide), and the remaining water is added to the emulsion to bring the formulation up to the desired volume. The resulting mixture is emulsified using, for example, a homogenizer to form the final emulsion. The emulsion can be filtered, and then transferred to the final containers. They can be sterilized by appropriate heat treatment in instances where such treatment does not cause significant and irreversible physical changes to the formulation.

Preferably, administration protocols are designed to minimize the formation of microbubbles due to volatility of the HVA. Microbubbles can result in reductions in end-tidal $CO_2$ and in the gradient of $CO_2$ between arterial and alveolar blood, especially in formulations containing more volatile HVAs such as desflurane. Such occurrences are more likely to occur when the emulsion is administered at room temperature than when the HVA-containing formulation is warmed to body temperature. Therefore, the formulation is preferably administered to the patient once it has been warmed to body temperature.

In addition, administration protocols should preferably avoid the use of negative pressure to withdraw doses from a multi-dose vial, since the concentration of HVA remaining in the vial may be changed due to the volatility of the HVA. However, with higher boiling anesthetics this may be less of a concern.

The following examples further illustrate the present invention, but of course, should not be construed as in any way limiting its scope.

Example 1

Preparation of Intravenous HVA Formulation

In this example, the preparation of a sevoflurane emulsion formulation is specifically described. Similar procedures are used for formulations containing enflurane, isoflurane and desflurane (see below).

Preparation of oil phase:
Take the tare weight of the vessel along with its mixing assembly.
Add refined soybean oil to it.
Heat the oil to approximately 50±5° C.
Add lecithin to the oil phase vessel.
Mix contents till lecithin is completely dissolved.
Bring the temperature of the oil/lecithin to about 22±2° C. and maintain this temperature.
Add the required amount of sevoflurane and maintain the temperature to 22±2° C.

Preparation of Aqueous Phase
Tare weight of the vessel along with its mixing assembly used for preparation of the aqueous phase.
Add the Water for Injection required to the aqueous phase vessel.
Add glycerin to the aqueous phase vessel.

Addition of Aqueous Phase to the Oil Phase
When ingredients in aqueous phase and oil phase are completely dissolved, transfer the aqueous phase into the oil phase.

Emulsification
Vigorously stir the primary emulsion for at least 10 minutes at 22±2° C. Observe the primary emulsion for homogeneity. Stop stirring once the emulsion appears uniform.

Cooling of Primary Emulsion
Assemble a ice-water cooling bath for cooling the primary emulsion. Cool the primary emulsion rapidly to ≦15° C., with constant stirring.

Homogenization

Pass the primary emulsion 3 times through the homogenizer at 14,500 psi. An ice water bath is used to cool the emulsion during this step.

Collect the final pass into a clean dry container.

Fill the emulsion into individual final containers under nitrogen cover.

TABLE 2

| Ingredient | mg/mL |
| --- | --- |
| Super Refined Soybean oil, USP | 200.00 |
| Sevoflurane (finished product) | 80.00 |
| Glycerin, USP/NF | 22.50 |
| Lecithin, Lipoid E 80 | 24.00 |
| Sterile water for Inj. USP/NF q.s. to, mL | 1.00 |

After the formulation was complete, actual recovery of the sevoflurane in the formulation was determined by gas chromatography analysis to be 7.0% w/v.

The procedures for other intravenous formulations that included enflurane, and isoflurane were identical to that used with sevoflurane.

The procedure was also conducted in a similar manner with desflurane except that additional cooling provisions were provided due to desflurane's lower boiling point. In particular, the oil phase was cooled and maintained at 2-5° C. when mixed with desflurane; the aqueous phase was cooled to 2-5° C. before combination with the oil phase; and the emulsion is maintained at 2-5° C. in the subsequent processing steps.

Table 3 indicates the HVA target concentration and the actual HVA concentration after final formulation for the enflurane, isoflurane and desflurane formulations.

TABLE 3

| Anesthetic | Target Concentration in Emulsion | Actual Concentration in Emulsion |
| --- | --- | --- |
| Enflurane | 8% w/v | 7.0% w/v |
| Isoflurane | 8% w/v | 7.1% w/v |
| Desflurane | 12% w/v | 9.6% w/v |

These intravenous formulations were used in Example 2.

Example 2

Effect of Intravenous Desflurane, Enflurane, Isoflurane, and Sevoflurane on Myocardial Infarct Size in Rabbits These experiments were designed to characterize the effects of different HVAs (enflurane, isoflurane, sevoflurane, and desflurane) administered intravenously in an emulsion on myocardial infarct size following ischemia and reperfusion in rabbits.

General Preparation

Male New Zealand white rabbits weighing between 2.5 and 3.0 kg were anesthetized with intravenous sodium pentobarbital (30 mg/kg). Additional doses of pentobarbital were titrated as required to assure that pedal and palpebral reflexes were absent throughout the experiment. A tracheotomy was performed through a ventral midline incision, and the trachea was cannulated. The rabbits were ventilated with positive pressure using an air-oxygen mixture ($FiO_2$=0.33). Arterial blood gas tensions and acid-base status were maintained within a normal physiological range (pH 7.35-7.45, $PaCO_2$ 25-40 mmHg, and $PaO_2$ 90-150 mmHg) by adjusting the respiratory rate or tidal volume. Body temperature was maintained with a heating blanket. Heparin-filled catheters were inserted into the right carotid artery and the left jugular vein for measurement of arterial blood pressure and fluid or drug administration, respectively. Maintenance fluids consisted of 0.9% saline (15 ml/kg/h) that were continued for the duration of the experiment.

A left thoracotomy was performed at the fourth intercostal space, and the heart was suspended in a pericardial cradle. A prominent branch of the left anterior descending coronary artery (LAD) was selected, and a silk ligature was placed around this artery approximately halfway between the base and apex for the production of coronary artery occlusion and reperfusion in myocardial infarct size experiments. Each rabbit was anticoagulated with 500 U of heparin immediately before LAD occlusion. Coronary artery occlusion was verified by the presence of epicardial cyanosis and regional dyskinesia in the ischemic zone, and reperfusion was confirmed by observing an epicardial hyperemic response. Hemodynamics were continuously recorded on a polygraph throughout experimentation. After the surgical preparation, 30 min of stabilization were allowed.

Experimental Design

Figure 1:
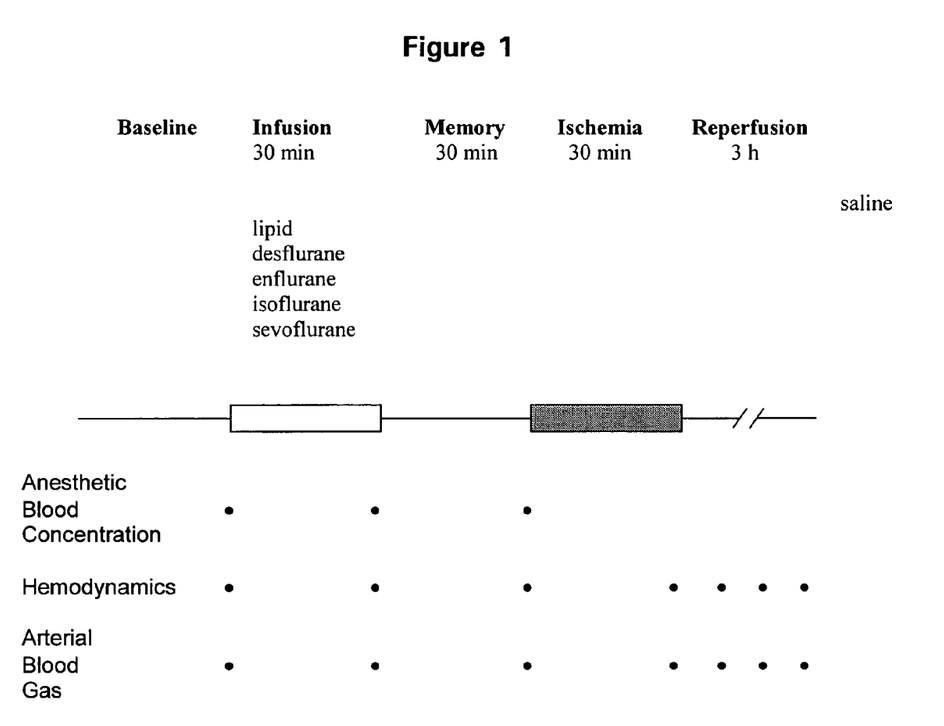
FIG. 1 is a schematic illustration of an experimental protocol used in determining myocardial infarct size in rabbits.

The experimental design for the experiments is illustrated in FIG. 1. Rabbits were randomly assigned to one of six experimental groups: a control group (0.9% saline infusion), a vehicle group (drug lipid vehicle), or one of four anesthetic groups (emulsified desflurane, isoflurane, enflurane, or sevoflurane). The vials of anesthetics were stored at 4° C. as prepared in Example 1. After opening, the vial was left in a water bath at 37° C. for 2 h. Anesthetics were directly poured into the syringe without using negative pressure suction.

Baseline measurements of systemic hemodynamics, arterial blood gas tensions, and blood concentrations of anesthetic agent were performed 30 min after instrumentation was completed. Rabbits received 0.9% saline, drug lipid vehicle (10 ml/h), or intravenous volatile anesthetic (10 ml/h) for 30 min. Infusions were discontinued 30 min prior to coronary occlusion (memory period). Blood concentrations of anesthetic agents were performed at baseline, at the end of anesthetic infusion, and at the end of the memory period just before coronary occlusion). HVA concentrations in blood were determined by gas chromatographic (GC) analysis. All rabbits underwent a 30 min LAD occlusion followed by 3 h reperfusion.

Determination of Myocardial Infarct Size

At the end of each experiment, the LAD was reoccluded and 3 ml of Patent blue dye was injected intravenously. The left ventricular area at risk for infarction was separated from surrounding normal areas (stained blue), and the two regions were incubated at 37° C. for 20 to 30 min in 1% 2,3,5-triphenyltetrazolium chloride in 0.1 M phosphate buffer adjusted to pH 7.4. After overnight storage in 10% formaldehyde, infarcted and noninfarcted myocardium within the area at risk were carefully separated and weighed. Infarct size was expressed as a percentage of the area at risk. Rabbits that developed intractable ventricular fibrillation and those with an area at risk less than 15% of LV mass were excluded from subsequent analysis.

Statistical Analysis

Statistical analysis of data within and between groups was performed with analysis of variance (ANOVA) for repeated measures followed by Student-Newman-Keuls test. Changes between groups were considered statistically significant when the p value was less than 0.05. All data are expressed as mean±SEM.

Results

General Consideration

All anesthetics were used under equivalent experimental conditions, as indicated previously (i.e., warmed for two hours at body temperature before infusion).

In the case of desflurane it was observed that bubbles accumulated in the syringe and extension tubing during the slow warming in the preparation of desflurane. Despite efforts to remove the bubbles, it was impossible to eliminate all bubbles, and some were likely infused during the infusion period. Desflurane results should therefore be interpreted with the constraints of this experimental limitation.

Hemodynamics

Hemodynamic data for each experimental group is shown in Table 4. There were no differences in heart rate between experimental groups. There was a decrease in mean arterial pressure (MAP) during the memory period of desflurane-treated as compared to control rabbits. MAP increased during the baseline and infusion periods in sevoflurane-treated compared to control rabbits. MAP decreased during the infusion period in isoflurane group. The rate-pressure product, an indirect index of myocardial oxygen consumption, decreased after 1 hr of reperfusion in rabbits receiving desflurane and isoflurane.

respectively. There were no changes in pH, $PaO_2$ or end-tidal $CO_2$ between experimental groups.

Blood concentrations as measured by GC were converted to their MAC-equivalent values by calculations described below. Initially "n", or the number of moles of HVA in 1 L of alveolar gas during exposure to 1.0 MAC of the HVA was calculated. The ideal gas law n=PV/RT is used to calculate the number of moles of HVA present at 1 MAC in the alveolar gas where: V=1 L, T=273+37=310° (K); and R=0.0821 (universal gas constant). P or pressure was determined taking into account the vapor pressure of water at 37° C. which is 47.1 torr, and the volume percent of the HVA. Volume percentages of HVAs (MAC values) were obtained from literature values determined in rabbits (Scheller et al. Can. J. Anaesth. 1988, 35: 133-136; Drummond, J C Anesthesiology 1985; 62: 336-8, and Doorley et al. Anesthesiology 1988; 69, 89-91), and are presented in Table 8.

The number of moles of the HVA in 1 L at 37° C. at 1 MAC in rabbits was then used to determine the concentration of the HVA present in blood by using known blood/gas partition values (also known as λ). Blood gas partition values for the HVAs used in the study are show in Table 8. The value for "x" (or the equivalent blood concentration of the HVA at 1 MAC at 37° C. in rabbit) is then determined by the equation:

$$x = \lambda n$$

TABLE 4

Systemic Hemodynamics

| | Baseline | Infusion | Memory | Ischemia 30 min | Reperfusion (h) | | |
| --- | --- | --- | --- | --- | --- | --- | --- |
| | | | | | 1 | 2 | 3 |
| HR (bpm) | | | | | | | |
| CONTROL | 250 ± 8 | 250 ± 8 | 250 ± 8 | 240 ± 6 | 229 ± 4 | 221 ± 4 | 215 ± 5 |
| VEHICLE | 235 ± 15 | 247 ± 10 | 250 ± 10 | 236 ± 14 | 232 ± 15 | 222 ± 14 | 219 ± 14 |
| DES | 261 ± 11 | 253 ± 9 | 231 ± 9 | 228 ± 7 | 201 ± 14 | 216 ± 6 | 219 ± 7 |
| ENF | 248 ± 10 | 240 ± 11 | 231 ± 11 | 213 ± 9 | 216 ± 7 | 214 ± 10 | 210 ± 7 |
| ISO | 240 ± 9 | 227 ± 14 | 229 ± 10 | 220 ± 11 | 212 ± 4 | 201 ± 6 | 195 ± 7 |
| SEVO | 227 ± 7 | 235 ± 9 | 227 ± 11 | 214 ± 8 | 206 ± 9 | 193 ± 10 | 188 ± 9 |
| MAP (mmHg) | | | | | | | |
| CONTROL | 82 ± 3 | 82 ± 3 | 82 ± 3 | 66 ± 2 | 69 ± 3 | 66 ± 4 | 66 ± 3 |
| VEHICLE | 73 ± 4 | 74 ± 5 | 70 ± 5 | 56 ± 6 | 58 ± 6 | 57 ± 4 | 54 ± 4 |
| DES | 71 ± 8 | 67 ± 9 | 58 ± 10* | 53 ± 8 | 54 ± 7 | 58 ± 8 | 54 ± 5 |
| ENF | 78 ± 4 | 68 ± 3 | 70 ± 3 | 59 ± 6 | 65 ± 6 | 68 ± 7 | 75 ± 5 |
| ISO | 64 ± 5 | 57 ± 6* | 62 ± 6 | 54 ± 5 | 52 ± 3 | 54 ± 3 | 58 ± 3 |
| SEV | 92 ± 4* | 91 ± 4* | 87 ± 4 | 64 ± 5 | 65 ± 3 | 65 ± 3 | 65 ± 2 |
| RPP (bpm × mmHg × $10^3$) | | | | | | | |
| CONTROL | 22.9 ± 1.0 | 22.9 ± 1.0 | 22.9 ± 1.0 | 18.3 ± 0.7 | 18.1 ± 0.8 | 16.4 ± 0.7 | 15.9 ± 0.7 |
| VEHICLE | 19.7 ± 1.5 | 20.5 ± 1.3 | 19.9 ± 1.4 | 15.3 ± 1.6 | 15.8 ± 1.6 | 15 ± 1.3 | 13.7 ± 1.1 |
| DES | 21.3 ± 3 | 20.4 ± 2.8 | 16.3 ± 3 | 14.5 ± 2 | 12.4 ± 0.4* | 15 ± 2.1 | 14.2 ± 1.4 |
| ENF | 22 ± 1.9 | 18.9 ± 1.5 | 18.9 ± 1.4 | 14.5 ± 1.7 | 15.8 ± 1.5 | 16.5 ± 1.6 | 17.6 ± 1.3 |
| ISO | 17.7 ± 2 | 16.2 ± 2.2 | 16.7 ± 2 | 14.3 ± 1.6 | 13.3 ± 0.8* | 13.2 ± 1 | 13.5 ± 1 |
| SEV | 22.9 ± 1.3 | 23.7 ± 1.7 | 22.1 ± 1.8 | 15.7 ± 1.6 | 15.2 ± 1.3 | 14 ± 1.2 | 13.8 ± 0.8 |

Data are mean ± SEM.
*significantly different from control group (p < 0.05).
HR = heart rate;
MAP = mean arterial blood pressure;
RPP = rate-pressure product.
DES = desflurane,
ENF = enflurane,
ISO = isoflurane,
SEV = sevoflurane.
n = 8 CONTROL, 7 VEHICLE, 7 DES, 8 ENF, 8 ISO, 8 SEVO.

Anesthetic Concentrations, Arterial Blood Gas Tensions and End-Tidal Gas Analysis Arterial blood gas tensions, end-tidal gas and anesthetic blood concentrations data are summarized in Tables 5-7, To express a measured blood concentration of an HVA as a MAC-equivalent value, the measured blood concentration is divided by x. The MAC equivalent values shown in Table 8 were calculated according to the above from the blood concentrations observed (see Table 7).

TABLE 8

| Anesthetic | Partition Coefficient ("λ") | Average MAC, % v/v | 1 MAC-Equivalent Blood Concentration (mM) at 1 MAC ("x") | Observed Blood Concentration following 30 min, 10 mL/h Infusion, mM | Observed Blood Concentration following 30 min, 10 mL/h Infusion, MAC-Equivalents |
|---|---|---|---|---|---|
| Desflurane | 0.42 | 8.9 | 1.38 | 0.18 | 0.13 |
| Enflurane | 1.9 | 2.86 | 1.995 | 0.31 | 0.15 |
| Isoflurane | 1.4 | 2.05 | 1.06 | 0.18 | 0.17 |
| Sevoflurane | 0.69 | 3.7 | 0.94 | 0.15 | 0.16 |

TABLE 5

Arterial Blood Gas Analysis

| | Baseline | Infusion | Memory | Ischemia 30 min | Reperfusion (h) 1 | 2 | 3 |
|---|---|---|---|---|---|---|---|
| pH | | | | | | | |
| CONTROL | 7.43 ± 0.01 | 7.43 ± 0.01 | 7.43 ± 0.01 | 7.41 ± 0.02 | 7.39 ± 0.01 | 7.40 ± 0.01 | 7.42 ± 0.01 |
| VEHICLE | 7.47 ± 0.01 | 7.43 ± 0.03 | 7.41 ± 0.04 | 7.40 ± 0.03 | 7.41 ± 0.02 | 7.40 ± 0.01 | 7.40 ± 0.01 |
| DES | 7.45 ± 0.02 | 7.40 ± 0.02 | 7.36 ± 0.02 | 7.34 ± 0.01 | 7.37 ± 0.02 | 7.40 ± 0.01 | 7.41 ± 0.01 |
| ENF | 7.47 ± 0.02 | 7.41 ± 0.02 | 7.40 ± 0.02 | 7.37 ± 0.02 | 7.38 ± 0.02 | 7.40 ± 0.03 | 7.42 ± 0.02 |
| ISO | 7.43 ± 0.02 | 7.40 ± 0.03 | 7.36 ± 0.02 | 7.36 ± 0.02 | 7.39 ± 0.02 | 7.39 ± 0.02 | 7.39 ± 0.01 |
| SEVO | 7.44 ± 0.01 | 7.42 ± 0.01 | 7.39 ± 0.01 | 7.38 ± 0.01 | 7.39 ± 0.01 | 7.40 ± 0.01 | 7.39 ± 0.01 |
| $PaO_2$ (mmHg) | | | | | | | |
| CONTROL | 144 ± 14 | 144 ± 14 | 144 ± 14 | 112 ± 11 | 130 ± 9 | 145 ± 10 | 145 ± 10 |
| VEHICLE | 145 ± 13 | 139 ± 10 | 144 ± 15 | 144 ± 12 | 161 ± 10 | 168 ± 11 | 170 ± 7 |
| DES | 158 ± 23 | 157 ± 17 | 143 ± 17 | 136 ± 24 | 141 ± 19 | 155 ± 18 | 165 ± 12 |
| ENF | 151 ± 16 | 130 ± 14 | 149 ± 16 | 157 ± 22 | 143 ± 11 | 135 ± 10 | 131 ± 12 |
| ISO | 136 ± 17 | 124 ± 11 | 146 ± 15 | 166 ± 24 | 167 ± 12 | 169 ± 12 | 160 ± 13 |
| SEVO | 125 ± 8 | 118 ± 6 | 107 ± 11 | 106 ± 12 | 120 ± 7 | 127 ± 6 | 121 ± 8 |
| $PaCO_2$ (mmHg) | | | | | | | |
| CONTROL | 35 ± 2 | 35 ± 2 | 35 ± 2 | 35 ± 3 | 34 ± 3 | 33 ± 2 | 32 ± 2 |
| VEHICLE | 32 ± 1 | 36 ± 4 | 39 ± 5 | 36 ± 3 | 33 ± 2 | 34 ± 2 | 32 ± 2 |
| DES | 29 ± 2* | 32 ± 3 | 34 ± 3 | 31 ± 3 | 30 ± 4 | 26 ± 3* | 30 ± 1* |
| ENF | 28 ± 2* | 31 ± 2 | 30 ± 2 | 32 ± 2 | 28 ± 2 | 27 ± 2* | 32 ± 3 |
| ISO | 34 ± 2 | 34 ± 2 | 36 ± 2 | 33 ± 2 | 31 ± 2 | 32 ± 2 | 33 ± 2 |
| SEVO | 37 ± 1 | 38 ± 1 | 41 ± 1 | 40 ± 1 | 38 ± 1 | 38 ± 1 | 39 ± 1 |

Data are mean ± SEM.
*significantly different from control group ($p < 0.05$).
DES = desflurane,
ENF = enflurane,
ISO = isoflurane,
SEV = sevoflurane.
n = 8 CONTROL, 7 VEHICLE, 7 DES, 8 ENF, 8 ISO, 8 SEVO.

TABLE 6

End-tidal Gas Analysis

| | Baseline | Infusion | Memory | Ischemia 30 min | Reperfusion (h) 1 | 2 | 3 |
|---|---|---|---|---|---|---|---|
| $EtCO_2$ (mmHg) | | | | | | | |
| CONTROL | 36 ± 2 | 36 ± 2 | 36 ± 2 | 34 ± 3 | 35 ± 3 | 32 ± 2 | 33 ± 3 |
| VEHICLE | 34 ± 1 | 33 ± 1 | 33 ± 2 | 31 ± 2 | 31 ± 2 | 32 ± 2 | 32 ± 2 |
| DES | 31 ± 2 | 30 ± 2 | 28 ± 3 | 26 ± 3 | 29 ± 4 | 28 ± 3 | 29 ± 3 |
| ENF | 36 ± 2 | 37 ± 2 | 34 ± 2 | 33 ± 3 | 33 ± 3 | 33 ± 3 | 35 ± 3 |
| ISO | 34 ± 1 | 34 ± 1 | 33 ± 2 | 30 ± 2 | 27 ± 2 | 28 ± 2 | 30 ± 2 |
| SEVO | 35 ± 1 | 36 ± 1 | 36 ± 1 | 35 ± 1 | 34 ± 1 | 33 ± 1 | 34 ± 1 |
| EtHalogenated (%) | | | | | | | |
| CONTROL | — | — | — | — | — | — | — |
| VEHICLE | — | — | — | — | — | — | — |
| DES | 0 | 0.37 ± 0.03# | 0.03 ± 0.01 | 0.01 ± 0.00 | 0.00 ± 0.00 | 0.00 ± 0.00 | 0.00 ± 0.00 |

TABLE 6-continued

End-tidal Gas Analysis

| | Baseline | Infusion | Memory | Ischemia 30 min | Reperfusion (h) | | |
|---|---|---|---|---|---|---|---|
| | | | | | 1 | 2 | 3 |
| ENF | 0 | 0.27 ± 0.02 | 0.02 ± 0.01 | 0.00 ± 0.00 | 0.00 ± 0.00 | 0.00 ± 0.00 | 0.00 ± 0.00 |
| ISO | 0 | 0.31 ± 0.02 | 0.02 ± 0.01 | 0.00 ± 0.00 | 0.00 ± 0.00 | 0.00 ± 0.00 | 0.00 ± 0.00 |
| SEVO | 0 | 0.34 ± 0.02 | 0.07 ± 0.01 | 0.04 ± 0.01 | 0.03 ± 0.01 | 0.04 ± 0.01 | 0.05 ± 0.01 |

Data are mean ± SEM.
significantly different from enflurane group (p < 0.05).
DES = desflurane,
ENF = enflurane,
ISO = isoflurane,
SEV = sevoflurane.
n = 8 CONTROL, 7 VEHICLE, 7 DES, 8 ENF, 8 ISO, 8 SEVO.

TABLE 7

Blood Concentration of Anesthetics

| | Baseline Blood Concentration (mM) | Infusion | Memory |
|---|---|---|---|
| DES | 0 | 0.18 ± 0.03# | 0.03 ± 0.02 |
| ENF | 0 | 0.31 ± 0.03 | 0.06 ± 0.01 |

TABLE 7-continued

Blood Concentration of Anesthetics

| | Baseline Blood Concentration (mM) | Infusion | Memory |
|---|---|---|---|
| ISO | 0 | 0.18 ± 0.06# | 0.04 ± 0.02 |
| SEVO | 0 | 0.15 ± 0.01# | 0.02 ± 0.00# |

Data are mean ± SEM.
significantly different from enflurane group (p < 0.05).
DES = desflurane,
ENF = enflurane,
ISO = isoflurane,
SEV = sevoflurane.
n = 7 DES, 8 ENF, 8 ISO, 8 SEVO.

Infarct Size

Figure 2:
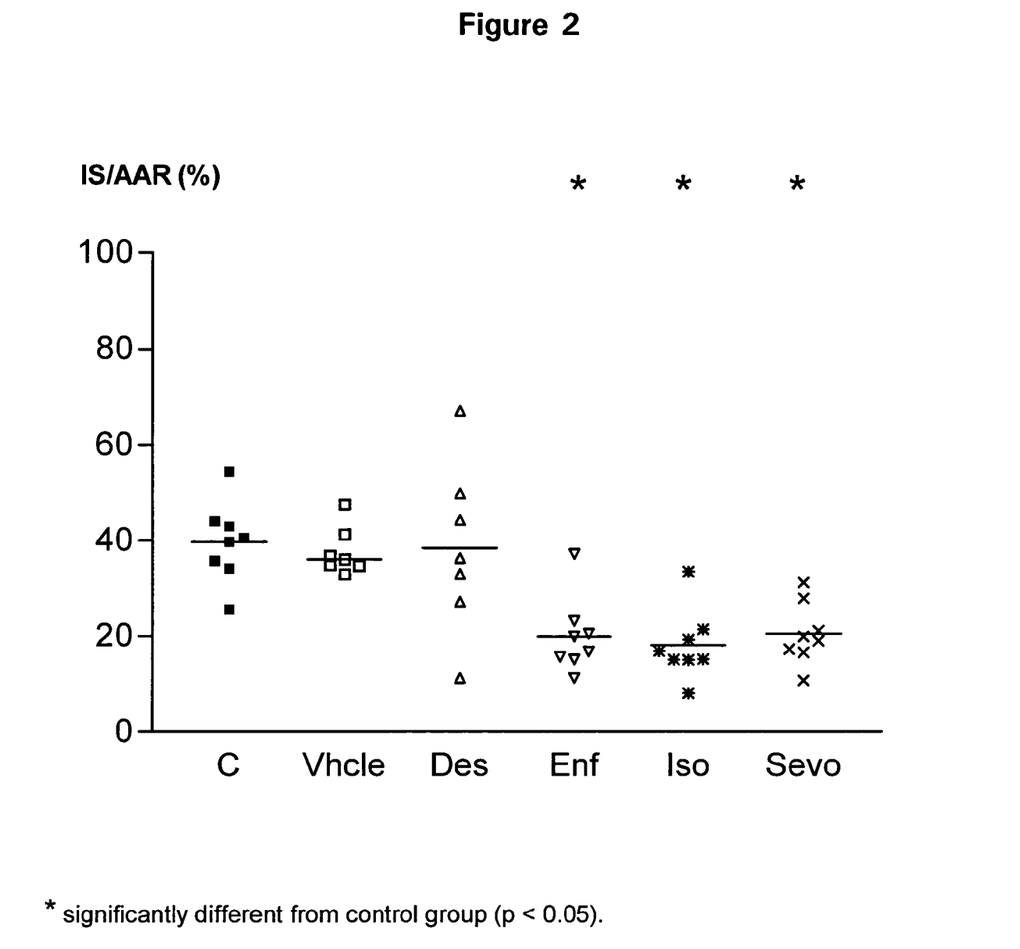
FIG. 2 indicates infarct size (IS) expressed as a percentage of area at risk (AAR) for each animal.
Figure 3:
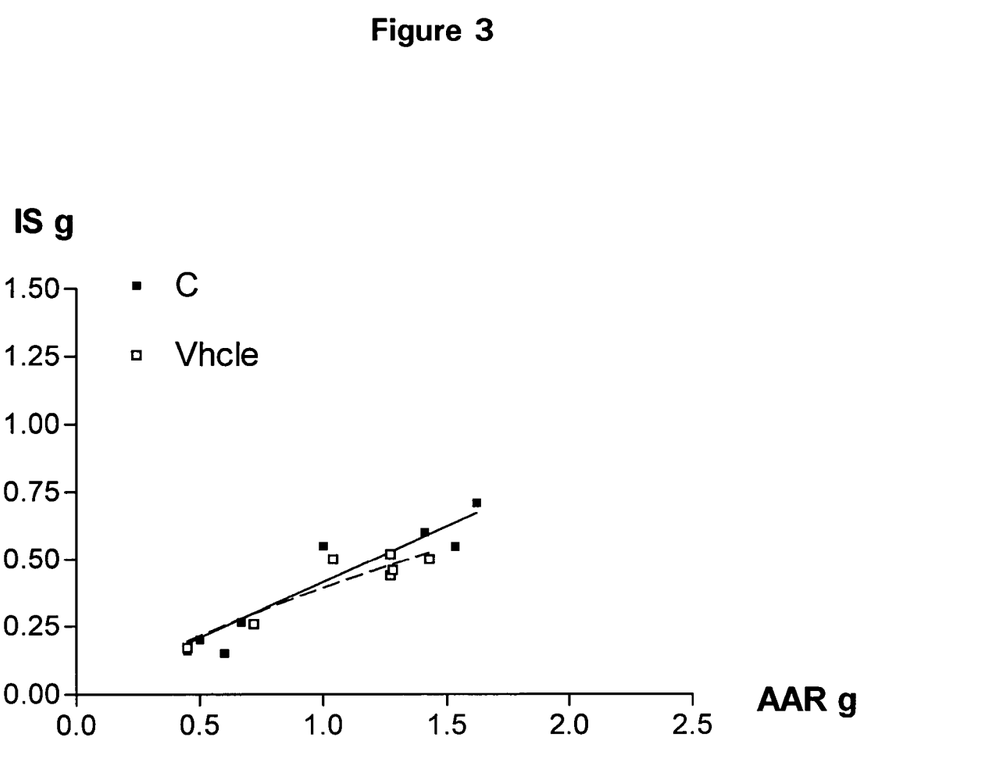
FIG. 3 is a graph indicating the infarct size (IS) plotted as a function of area at risk (AAR) for vehicle-treated animals. Each point represents one individual experiment.
Figure 4:
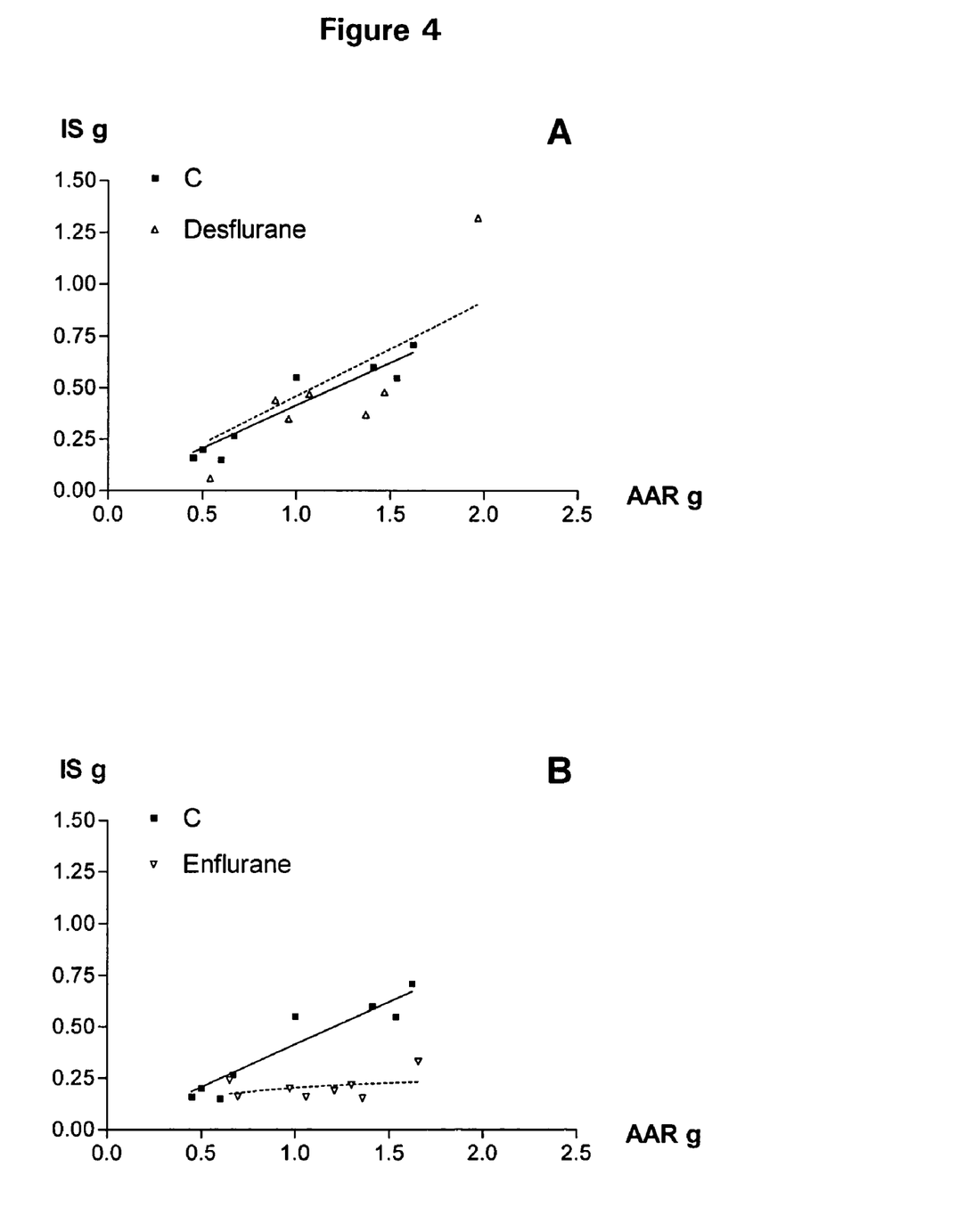
FIG. 4A is a graph indicating the infarct size (IS) plotted as a function of area at risk (AAR) for desflurane-treated animals. Each point represents one individual experiment.
FIG. 4B is a graph indicating the infarct size (IS) plotted as a function of area at risk (AAR) for enflurane-treated animals. Each point represents one individual experiment.
Figure 5:
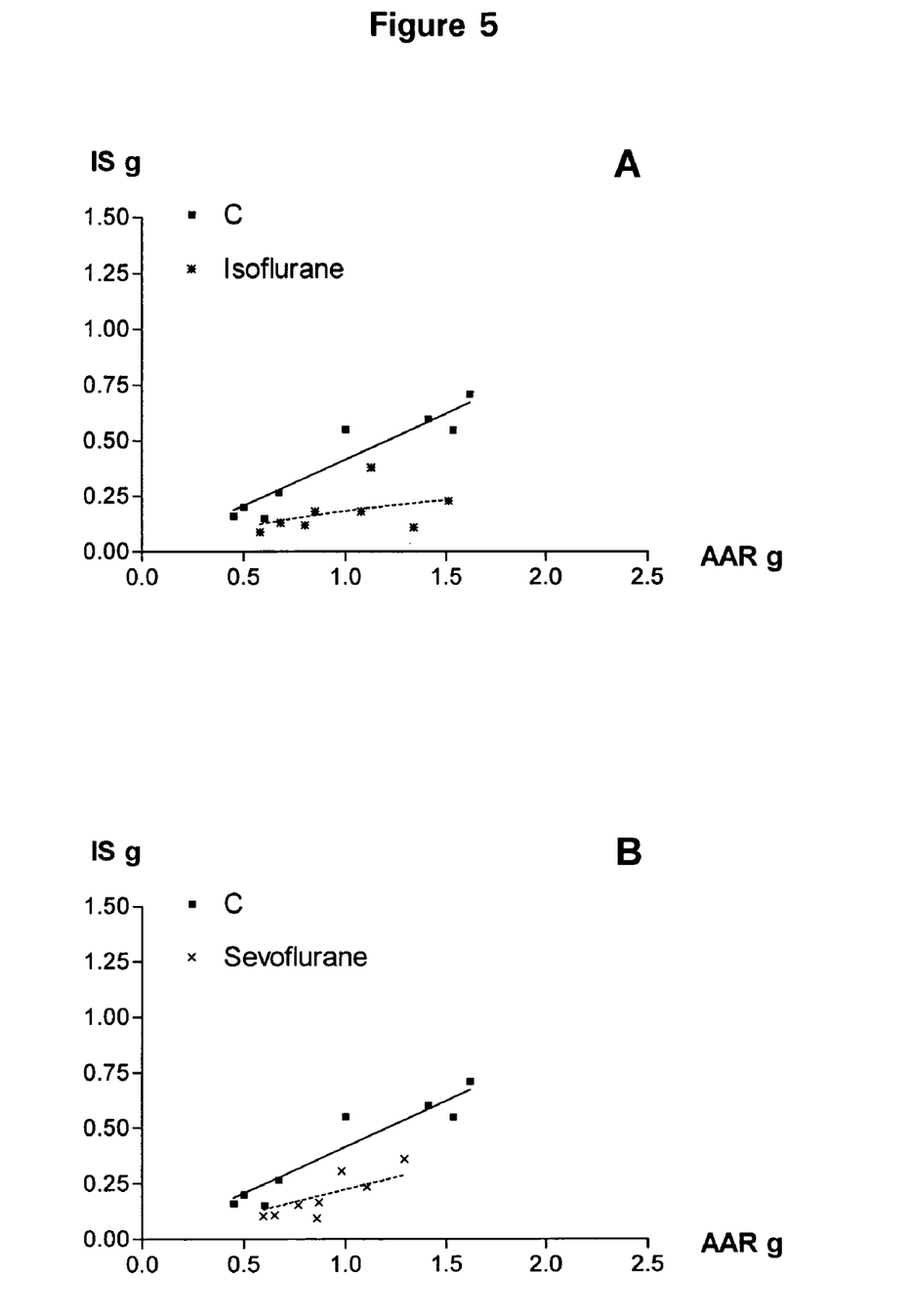
FIG. 5A is a graph indicating the infarct size (IS) plotted as a function of area at risk (AAR) for isoflurane-treated animals. Each point represents one individual experiment.
FIG. 5B is a graph indicating the infarct size (IS) plotted as a function of area at risk (AAR) for sevoflurane-treated animals. Each point represents one individual experiment.

Body weight, left ventricular weight, area at risk weight, and area at risk/left ventricular mass were similar between groups (Table 9). Enflurane, isoflurane and sevoflurane provided protection against myocardial ischemia-reperfusion injury (FIG. 2). Conversely, emulsified desflurane was unable to confer cardioprotection (a portion of desflurane's inability to do so may be related to the volatile anesthetic leaving the emulsion). These results were also confirmed by plotting the weight of the infarct size as a function of the weight of the area at risk (FIGS. 3, 4A, 4B, 5A and 5B). Lipid emulsion infusion had no effect on myocardial sensitivity to ischemia-reperfusion injury, as indicated by FIG. 3. All points in the desflurane group lie close to the control regression line, indicating that for any value of area at risk, the desflurane group developed infarct size comparable to controls (FIG. 4A). Data points for enflurane, isoflurane, and sevoflurane groups lie markedly below the control line, indicating that for any size of the risk region, infarcts were smaller than in the control group (FIGS. 4B, 5A and 5B).

TABLE 9

Area at Risk Data

| | N | Body Weight (g) | LV WT (g) | AAR WT (g) | IF WT (g) | AAR/LV (%) | IF/AAR (%) |
|---|---|---|---|---|---|---|---|
| CONTROL | 8 | 2819 ± 89 | 3.29 ± 0.10 | 0.97 ± 0.17 | 0.40 ± 0.08 | 28.9 ± 4.5 | 39.7 ± 3.0 |
| VEHICLE | 7 | 2702 ± 48 | 3.35 ± 0.17 | 1.06 ± 0.13 | 0.41 ± 0.05 | 31.4 ± 3.3 | 38.4 ± 1.7 |
| DES | 7 | 2720 ± 90 | 2.73 ± 0.14 | 1.18 ± 0.18 | 0.50 ± 0.15 | 42.9 ± 5.5 | 38.5 ± 6.7 |
| ENF | 8 | 2755 ± 49 | 3.05 ± 0.13 | 1.11 ± 0.12 | 0.21 ± 0.02 | 36.2 ± 3.3 | 20.0 ± 2.8*# |
| ISO | 8 | 3071 ± 187 | 3.48 ± 0.18 | 0.99 ± 0.12 | 0.18 ± 0.03 | 28.2 ± 2.5 | 18.1 ± 2.6*# |
| SEVO | 8 | 2677 ± 54 | 2.76 ± 0.09 | 0.89 ± 0.08 | 0.19 ± 0.04 | 32.3 ± 2.8 | 20.5 ± 2.3*# |

Data are mean ± SEM.
*significantly different from control group.
significantly different from desflurane group, (p < 0.05)
DES = desflurane,
ENF = enflurane,
ISO = isoflurane,
SEV = sevoflurane.

These results strongly suggest that the HVAs enflurane, isoflurane and sevoflurane provide adequate protection against myocardial ischemia-reperfusion injury when administered intravenously in an emulsion, in this rabbit in vivo model. It is significant to note that such cardioprotection is achieved at blood concentrations that are ≦0.17 MAC-equivalents.

While the present data indicate that the desflurane formulation did not confer cardioprotection in this study, it is noted that this particular formulation may not be optimized for intravenous delivery of desflurane. As indicated above, bubbles formed upon warming the desflurane to body temperature for intravenous administration. The cardioprotection results for desflurane should therefore be interpreted in light of these observations. It may be possible that other intravenous formulations or other injection techniques may overcome the difficulties observed with desflurane.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A method of treating a patient having a tissue that is subject to an ischemic event, comprising:
    parentally administering a sub-anesthetic amount of a formulation comprising a halogenated volatile anesthetic to a patient having a tissue that is subject to an ischemic event, wherein the sub-anesthetic amount is effective to improve the tissue's resistance to or tolerance or the ischemic event.
2. The method of claim 1, wherein the formulation administered further comprises an emulsification adjuvant and an emulsifier.
3. The method of claim 1, wherein the tissue is selected from heart, brain, vasculature, gut, liver, kidney and eye.
4. The method of claim 1, wherein the ischemic event is selected from aortic aneurysm repair, multiple trauma, peripheral vascular disease, renal vascular disease, myocardial infarction, stroke, sepsis and multi-organ failure.
5. The method of claim 1, wherein the administration is conducted prior to the ischemic event.
6. The method of claim 1, wherein the administration is conducted concomitantly with the ischemic event.
7. The method of claim 1, wherein the administration is conducted after the ischemic event.
8. The method of claim 1, wherein the administration comprises bolus administration of the formulation.
9. The method of claim 1, wherein the administration comprises continuous infusion of the formulation.
10. The method of claim 1, wherein the halogenated volatile anesthetic is selected from the group consisting of desflurane, isoflurane, enflurane, halothane and sevoflurane.
11. The method of claim 1, wherein the tissue is heart tissue.
12. The method of claim 1, wherein the patient is in need of cardioprotection.
13. The method of claim 1, wherein the patient is in need of neuroprotection.

* * * * *

UNITED STATES PATENT AND TRADEMARK OFFICE
CERTIFICATE OF CORRECTION

PATENT NO. : 7,999,011 B2
APPLICATION NO. : 10/682303
DATED : August 16, 2011
INVENTOR(S) : Raul Trillo et al.

It is certified that error appears in the above-identified patent and that said Letters Patent is hereby corrected as shown below:

In the Claims:

At Column 17, line 10, "parentally" should be -- parenterally --

At Column 17, line 14, "improve the tissue's resistance to or tolerance or the" should be -- improve the tissue's resistance to or tolerance of the --

Signed and Sealed this
Fourth Day of June, 2013

Teresa Stanek Rea
*Acting Director of the United States Patent and Trademark Office*